(12) United States Patent
Slotman

(10) Patent No.: US 8,577,620 B2
(45) Date of Patent: Nov. 5, 2013

(54) METHODS FOR ASSESSING DRUG EFFICACY AND RESPONSE OF PATIENT TO THERAPY

(76) Inventor: Gus J. Slotman, Moorestown, NJ (US)

( * ) Notice: Subject to any disclaimer, the term of this patent is extended or adjusted under 35 U.S.C. 154(b) by 55 days.

(21) Appl. No.: 13/110,265

(22) Filed: May 18, 2011

(65) Prior Publication Data

US 2011/0238321 A1 Sep. 29, 2011

Related U.S. Application Data

(63) Continuation-in-part of application No. 12/749,977, filed on Mar. 30, 2010, now abandoned, which is a continuation of application No. 12/056,367, filed on Mar. 27, 2008, now abandoned.

(51) Int. Cl.
*G06F 19/00* (2011.01)
*G01N 33/53* (2006.01)

(52) U.S. Cl.
USPC .............................. 702/19; 435/7.1; 435/7.92

(58) Field of Classification Search
None
See application file for complete search history.

(56) References Cited

U.S. PATENT DOCUMENTS

| | | | |
|---|---|---|---|
| 6,190,872 B1 * | 2/2001 | Slotman | 435/7.92 |
| 2003/0104453 A1 | 6/2003 | Pickar et al. | 435/6 |
| 2003/0113831 A1 * | 6/2003 | Hakonarson | 435/29 |
| 2003/0211518 A1 | 11/2003 | Slotman | 435/6 |
| 2005/0143298 A1 | 6/2005 | Whitehouse | 514/9.1 |

OTHER PUBLICATIONS

Bernard et al. "Efficacy and Safety of Recombinant Human Activated Protein C for Severe Sepsis" New England Journal of Medicine 2001 344(10):699-709.

Bone, R. C. "Gram-negative Sepsis: A Dilemma of Modern Medicine" Clinical Microbiology Reviews 1993 6(1):57-68.
Bone, R. C. "The Pathogenesis of Sepsis" Annals of Internal Medicine 1991 115:457-469.
Craddock et al. "Complement (C5a)—induced Granulocyte Aggregation in vitro" Journal of Clinical Investigations 1977 60:260-264.
Fisher et al. "Recombinant Human Interleukin 1 Receptor Antagonist in the Treatment of Patients with Sepsis Syndrome" Journal of the American Medical Association 1994 271(23):1836-1843.
Green et al. "Analysis of Nitrate, Nitrite, and [$^{15}$N]NITRATE in Biological Fluids" Biochemistry 1982 126:131-138.
Hammerschmidt et al. "Granulocyte Aggregometry: A Sensitive Technique for the Detection of C5a and Complement Activation" Blood 1980 55(6):898-902.
Roumen et al. "Scoring Systems and Blood Lactate Concentration in Relation to the Development of Adult Respiratory Distress Syndrome and Multiple Organ Failure in Severely Traumatized Patients" The Journal of Trauma 1993 35(3):349-355.
Sauaia et al. "Early Predictors of Postinjury Multiple Organ Failure" Archives of Surgery 1994 129:39-45.
Slotman et al. "Prostaglandin and Complement Interaction in Clinical Acute Respiratory Failure" Archives of Surgery 1986 121:271-274.
Slotman et al. "Interaction of Prostaglandins, Activated Complement, and Granulocytes in Clinical Sepsis and Hypotension" Surgery 1986 99(6):744-750.
International Search Report from PCT/US2009/038337, May 9, 2009, PCT.

* cited by examiner

*Primary Examiner* — Lori A Clow
(74) *Attorney, Agent, or Firm* — Licata & Tyrrell P.C.

(57) ABSTRACT

Methods of identifying, monitoring and matching patients with appropriate treatments who are at risk for developing a systemic inflammatory condition using a systemic mediator-associated physiologic test profile are provided. The methods of the present invention increase the likelihood of demonstrating clinical efficacy in clinical trial datasets.

4 Claims, No Drawings

METHODS FOR ASSESSING DRUG EFFICACY AND RESPONSE OF PATIENT TO THERAPY

The instant patent application is a continuation-in-part of application Ser. No. 12/749,977 filed Mar. 30, 2010 now abandoned, which is a continuation of application Ser. No. 12/056,367, filed Mar. 27, 2008, now abandoned, both of which are incorporated herein in their entireties by reference.

INTRODUCTION

Background of the Invention

Since 1982, clinical trials of new drugs for sepsis have used, virtually unaltered, the entry criteria from the Solu-Medrol (methyprednisolone sodium succinate) study (Bone, et al. (1987) N. Engl. J. Med. 317:653-659). The Solu-Medrol definitions were first published in the report of that clinical trial's results. Subsequently, the placebo results were reported as sepsis syndrome (Bone, et al. (1989) Crit. Care Med. 17:389-393). Later, they were codified into medical culture by the American College of Chest Physicians/Society of Critical Care Medicine (ACCP/SCCM) Consensus Conference on sepsis (Bone, et al. (1992) Chest 101:1644-1655). Since the ACCP/SCCM Consensus Conference, sepsis definitions were published (Bone, et al. (1992) supra), and they have been used almost exclusively as the entry criteria for sepsis clinical trials. Unfortunately, in every sepsis clinical trial that has enrolled patients under those definitions, the study drug has failed to reduce septic mortality. Even the large investigations of an anti-tumor necrosis factor (TNF) antibody (Pulmonary Reviews.com (2000) vol. 5) and recombinant activated protein C (XIGRIS; Bernard, et al. (2001) N. Engl. J. Med. 344:699-709), while statistically significant, did not reduce septic mortality to levels that changed standards of care. The anti-TNF antibody was not approved by the Food and Drug Administration (FDA), and XIGRIS has been underutilized in the medical market.

Prospective, randomized, double-blind, placebo-controlled clinical trials are accepted universally as the highest level of scientific testing for potentially therapeutic molecules in sepsis. From the accumulated sepsis clinical trial data, then, the reasonable conclusion would be that the new drugs studied simply had no beneficial effects. However, it is also possible that novel sepsis therapies have failed to reduce septic mortality because they were not tested in a study population that was responsive to their biological effects. One might speculate that clinical trial entry criteria based on the ACCP/SCCM Consensus Conference publications and other clinical definitions of sepsis could have allowed such large numbers of patients to be enrolled in sepsis studies, whose host-inflammatory responses to infection were unable to benefit from the test compound that their treatment effects were lost within a nonspecific clinical trial population. The true target population for each sepsis drug, then, could be diluted to into invisibility by the overwhelming numbers of nonresponders enrolled. As a result, potentially life-saving drugs for sepsis and septic shock may not have received a fair chance to prove their efficacy but still were deemed ineffective because they were evaluated in what were otherwise thought to be well-designed clinical trials.

Accordingly, there is a need in the art for improved methods of evaluating clinical trial data and identifying subjects suitable for a particular clinical trial as well as identifying subjects, in a clinical setting, that will respond or gain benefit from a therapeutic drug.

SUMMARY OF THE INVENTION

The present invention features the use of systemic mediator-associated response test (SMART) models to predict clinical events in sepsis and other diseases or conditions. In one embodiment, the invention provides a method for analyzing clinical trials results for efficacy of a therapy for systemic inflammatory conditions by (a) obtaining one or more prerandomization baseline parameters of patients selected for a clinical trial for therapy of systemic inflammatory conditions; (b) generating from the prerandomization baseline parameters systemic mediator-associated response test (SMART) profiles for the patients receiving therapy; (c) using statistical tests to compare the SMART profiles of subjects of step (b) that responded or failed to respond to the therapy; and (d) producing a control profile indicative of response, including beneficial or detrimental, to the therapy.

In another embodiment, the invention provides a method for identifying a subject whose host-inflammatory responses to infection is matched to the mechanism of action of a therapeutic agent for the treatment of the subject by (a) obtaining one or more baseline parameters of subject with a systemic inflammatory condition; (b) generating from the baseline parameters a systemic mediator-associated response test (SMART) profile for the subject; (c) using statistical tests to compare the SMART profile of subject of step (b) with a SMART profile for a therapeutic agent with a predetermined mechanism of action; and (d) identifying whether the SMART profile of the subject matches the SMART profile of the therapeutic agent. In accordance with this embodiment, the predetermined mechanism of action of the therapeutic agent can include inhibiting tumor necrosis factor, inhibiting endotoxin activity, inhibiting interleukin-1 receptor, or degrading platelet-activating factor and oxidized phospholipids. In other embodiments, the subject is being treated for a systemic inflammatory condition or is in or being considered for a clinical trial.

DETAILED DESCRIPTION OF THE INVENTION

Methods for prognosticating clinical events in sepsis and other diseases or conditions have now been developed. The methods involve the generation of a systemic mediator-associated response test (SMART) model for a particular drug or patient using baseline data and objectively identifying subjects among whom novel treatments can, e.g., reduce septic mortality. By way of illustration, the studies described herein analyzed results of sepsis clinical trials that used consensus definitions as entry criteria, in which the study test molecule failed to reduce septic mortality. The results of this study illustrated SMART's ability to identify objectively, from pre-randomization baseline data, patients within failed clinical trials among whom novel treatments reduce septic mortality. SMART also predicted which sepsis drugs may not be beneficial. Specifically, SMART models uncovered cohorts of septic patients wherein E5, TNFMAb, and IL-1ra improved survival significantly. Furthermore, the SMART models built on the NORASEPT (North American Sepsis Trial) database, and efficacy of the TNFMAb study drug, were validated prospectively in NORASEPT II. Conversely, the failure of platelet-activation factor acetylhydrolase (PAF-AH) to lower septic mortality, and its possible adverse effects, was predicted early in the COMPASS (Controlled Mortality trial of human Platelet-activating factor Acetylhydrolase for treatment of Severe Sepsis) study database by SMART. However, even in maximally steroid-responsive SMART cohorts, hydrocortisone did not improve septic shock survival, neither in CORTICUS (Corticosteorid Treatment of Septic Shock) overall nor in corticotrophin non-responders. These results were achieved in clinical trial databases that were uncontrolled for optimal statistical modeling, and through analyzing only ordinary bedside observations and standard hospital laboratory tests, without the potentially valuable contributions of circulating levels of inflammatory response mediators or other sepsis biomarkers.

Treatments for systemic inflammatory conditions have failed to reach their full potential as early subclinical identification of appropriate patients to participate in clinical efficacy studies has proven most difficult. Physiologic scoring systems which are used by physicians to predict mortality in a patient have generally proven insufficient in predicting the onset of a systemic inflammatory condition subclinically. Accordingly, in one embodiment of the invention, SMART profiles are used in the analysis of clinical trial results for efficacy of a therapy for systemic inflammatory conditions. This method involves (a) obtaining one or more prerandomization baseline parameters of subjects selected for a clinical trial for therapy of systemic inflammatory conditions; (b) generating from the prerandomization baseline parameters systemic mediator-associated response test (SMART) profiles for the subjects receiving therapy; (c) using statistical tests to compare the SMART profiles of subjects of step (b) that responded or failed to respond to the therapy; and (d) producing a control profile indicative of response to the therapy.

The development of systemic inflammatory conditions represents a significant portion of the morbidity and mortality incidence which occur in the intensive care unit (ICU). The term "systemic inflammatory conditions" is used herein to describe conditions which result in a host response manifested by increased capillary permeability, organ failure, and death. Examples of systemic inflammatory conditions include, but are not limited to, ARDS, SIRS, sepsis, MODS, single organ dysfunction, shock, transplant rejection, cancer and trauma. Systemic inflammatory conditions such as ARDS, SIRS and MODS are responsible for more than 70% of the ventilator days spent on the ICU. In addition, ARDS, SIRS, sepsis and MODS are primary causes of death following surgery in surgical ICU patients, thus placing a heavy burden on the health care system. Generally, systemic inflammatory conditions do not develop in healthy individuals but rather in patients with preexisting severe disease or in persons who have suffered catastrophic acute illness or trauma. Patients at greatest risk of dying of a systemic inflammatory condition are the elderly; those receiving immunosuppressive drugs; and those with malignancies, cirrhosis, asplenia, or multiple underlying disorders (Bone (1991) *Annals of Internal Medicine* 115:457-469).

Accordingly, optimizing treatment for patients in this high risk group would be especially useful to clinicians. It must also be remembered that many sepsis patients were healthy before undergoing some type of trauma and as such healthy individuals who have undergone severe trauma and are now either at risk of developing sepsis or who have developed sepsis would also benefit from application of the present invention. Once a patient is identified as likely to respond based on comparison of his or her SMART profile to the SMART profile established in the clinical population that responded to treatment, the physician would employ their experience and judgment in determining the appropriate mode and timing of treatment.

Based upon the results presented herein, the methods of the present invention can be used to identify treatments that could be used successfully to treat patients with severe sepsis or any other similar systemic inflammatory condition. In this respect, methods are also provided for matching patients with other novel treatments based upon comparison of SMART profiles for the patient and established control profiles for effective treatments or new treatments with predetermined mechanisms of action (e.g., inhibiting tumor necrosis factor, inhibiting endotoxin activity, inhibiting interleukin-1 receptor, or degrading platelet-activating factor and oxidized phospholipids). By matching patients with treatments, effective treatments for patients at risk for developing a systemic inflammatory condition can be selected. The optimization of treatment for patient populations with the present method is an improvement on current methods of clinical trial data analysis and increases the likelihood that efficacy will be shown in the clinical trial. In this method, a SMART profile is generated for the subject from selected baseline parameters. The patient SMART profile is then compared with established control profiles for effective treatments or therapies with predetermined mechanisms of action. Selection of a treatment for the patient is based upon comparing and identifying the established control profiles for effective treatments which exhibit similarities to the patient's profile. In addition, appropriate patient populations for testing of new drugs in development can be selected via matching of patients with treatments based upon SMART profiles. By "appropriate patient population" it is meant subjects who meet the clinical entry criteria of a study for a new drug, and whose SMART profile matches that of a SMART profile for the new drug or a drug with a similar mechanism of action, such that the subject will likely respond positively to the new drug if randomized to it.

For purposes of this invention, a "control profile" or "clinical population profile" can be generated from a database containing mean values for selected patient parameters from a population of patients being treated for severe sepsis or septic shock. In other embodiments, a "control profile" can be generated from the same patient to compare and monitor changes in the patient parameters over time.

A control profile for effective treatment is a control profile, as defined supra, that is linked to a treatment identified to be effective in those patients with similar conditions and/or injuries from which the control profile was generated.

SMART profiles of the present invention are generated from one or more baseline or prerandomized baseline parameters. Patient parameters, for purposes of this invention, may include selected demographic variables, selected physiologic variables and/or results from selected standard hospital laboratory tests.

Exemplary demographic variables which may be selected for inclusion in a SMART profile include, but are not limited to, age, sex, race, comorbidities such as alcohol abuse, cirrhosis, HIV, dialysis, neutropenia, COPD, solid tumors, hematologic malignancies, chronic renal failure and the admitting service, i.e., surgery or medicine, and trauma.

Examples of physiologic variables which may be selected for inclusion in a SMART profile include, but are not limited to, physical examination, vital signs, hemodynamic measurements and calculations, clinical laboratory tests, concentrations of acute inflammatory response mediators, and endotoxin levels. More specifically, physiologic variables selected may include height, weight, temperature, MAP, heart rate, diastolic blood pressure, systolic blood pressure, mechanical ventilation, respiratory rate, pressure support, PEEP, SVR, cardiac index and/or PCWP of the patient. In addition, complete blood count, platelet count, prothrombin time, partial thromboplastin time, fibrin degradation products and D-dimer, serum creatinine, lactic acid bilirubin, AST, ALT, and/or GGT can be measured. Heart rate, respiratory rate, blood pressure and urine output can also be monitored. A full hemodynamic profile can also recorded in patients with pulmonary artery catheters and arterial blood gases are performed in patients on ventilators. Chest X-rays and bacterial cultures can also performed as clinically indicated. Examples of inflammatory response mediators which can be determined from a biological sample obtained from the patient include, but are not limited to, prostaglandin 6-keto F1α (PGI) (the stable metabolite of prostacyclin), thromboxane $B_2$ (TxB) (the stable metabolite of thromboxane $A_2$), leukotrienes $B_4$, $C_4$, $D_4$ and $E_4$, interleukin-6, interleukin-8, interleukin-1β, tumor necrosis factor, neutrophil elastase, complement components C3 and C5a, platelet activating factor, nitric oxide metabolites and endotoxin levels.

Exemplary hospital laboratory tests considered standard by those skilled in the art which may be selected for inclusion in a SMART profile include, but are not limited to, levels of albumin, alkaline phosphatase, ALT, AST, BUN, calcium, cholesterol, creatinine, GGT, glucose, hematocrit, hemoglobin, MCH, MCV, MCHC, phosphorus, platelet count, potassium, total protein, PT, PTT, RBC, sodium, total bilirubin, triglycerides, uric acid, WBCL, base deficit, pH, $PaO_2$, $SaO_2$, $FiO_2$, chloride, and lactic acid.

Some or all of these patient parameters are preferably determined at baseline (before drug treatment, drug intervention or before randomization to a clinical trial), and daily thereafter where applicable, and are entered into a database and a SMART profile comprising one or more of the patient parameters is generated from the database. As one of skill in the art will appreciate from this disclosure, as other additional patient parameters are identified which are predictive of a systemic inflammatory condition, they can also be incorporated into the database and as part of the SMART profile. Similarly, as SMART profiles are generated for more patients and additional data are collected for these parameters, it may be found that some parameters in this list of examples are less predictive than others. Those parameters identified as less predictive in a larger patient population need not be included in all SMART profiles.

Examples of biological samples from which some of these physiologic parameters are determined include, but are not limited to, blood, plasma, serum, urine, bronchioalveolar lavage, sputum, and cerebrospinal fluid.

As will be understood by those of skill in the art upon reading this disclosure, SMART profiles can be generated from all of the patient parameters discussed supra. Alternatively, SMART profiles can be based upon only a portion of the patient parameters. Since the patient parameters for each patient, as well as the control profiles or clinical population profile, are stored in a database, various SMART profiles comprising different patient parameters can be generated for a single patient and compared to an established control profile comprising the same parameters. The ability of these various profiles to be predictive can then be determined via statistical analysis.

Continuous, normally distributed variables are evaluated using analysis of variance. When appropriate, statistical comparisons between subgroups are made using the t-test or the chi-squared equation for categorical variables The physician or another individual of skill in the art uses the SMART profile as a guide to identifying patients that would respond or likely fail to respond to a particular treatment based upon whether the SMART profile of the patient matches the SMART profile of a therapeutic agent with a predetermined mechanism of action. In this respect, the SMART methodology can supplement clinical entry criteria for studies of antibiotics, cancer treatments, and transplant regimens, among others, as well as new drugs for sepsis, acute organ failure, and other systemic inflammatory conditions. SMART profiles ensure that the study drug receives a reasonable chance to demonstrate its efficacy in the conditions under treatment. After SMART profiling is used to demonstrate a drug's efficacy, SMART profiles can then be applied at the bedside to identify individual patients for whom the drug in question is beneficial. Using SMART, the host inflammatory response of individuals can now be matched to the biopharmacologic properties of a drug. This method is therefore a way to enhance the likelihood that clinical efficacy will be demonstrated in clinical trials.

The invention is further illustrated by the following non-limiting examples.

Example 1

Methods

The database from the second phase III clinical trial of the E5 anti-endotoxin antibody in sepsis (Bone, et al. (1995) supra) was supplied by XOMA LLC (Berkeley, Calif.). Data from the Synergen 0509 clinical trial of interleukin (IL)-1ra in sepsis (Fisher, et al. (1994) *JAMA* 271:1836-1843) were supplied by Amgen, Inc. (Thousand Oaks, Calif.). Data from the NORASEPT and NORASEPT II clinical trials (Abraham, et al. (1995) *JAMA* 273:934-941; Abraham, et al. (1998) *Lancet* 351:929-923) were supplied by the Bayer Corporation (West Haven, Conn.). Data from the COMPASS clinical trial of PAF-AH in sepsis (Opal, et al. (2004) *Crit. Care Med.* 32:332-341) were supplied by ICOS Corporation (Seattle, Wash.). The clinical trial database of the CORTICUS study (Sprung, et al. (2008) *N. Engl. J. Med.* 358:111-124) was supplied by Charles Sprung, M.D. Details of each of these clinical trials are summarized in Table 1.

TABLE 1

| Clinical Trial | Sponsor | Study Drug | Entry Criteria | Year Study Ended |
|---|---|---|---|---|
| E5 | XOMA | E5 anti-endotoxin-modified antibody | Sepsis syndrome | 1991 |
| NORASEPT | Bayer | TNFMAb antitumor necrosis factor monoclonal antibody | Sepsis syndrome | 1993 |
| NORASEPT II | Bayer | TNFMAb | Septic shock | 1998 |
| 0509 | Synergen | IL-1ra | Modified Sepsis syndrome | 1994 |
| COMPASS | ICOS | PAF-AH | Modified ACCP/SCCM consensus definitions of sepsis | 2004 |

TABLE 1-continued

| Clinical Trial | Sponsor | Study Drug | Entry Criteria | Year Study Ended |
|---|---|---|---|---|
| CORTICUS | Multiple | Hydrocortisone (50 mg IV every 6 hours for 5 days) | Modified ACCP/SCCM Consensus Definitions of Septic Shock | 2005 |

No patient-identifying information was included. The NORASEPT and NORASEPT II studies were sequential multi-institutional studies of TNFMAb in severe sepsis and septic shock. All investigations were prospective, randomized, double blind, placebo-controlled phase III clinical trials. In the E5 study, the primary end point was a 30-day all-cause mortality (Bone, et al. (1995) supra). The primary end point in the NORASEPT and NORASEPT II, Synergen 0509, COMPASS and CORTICUS studies was 28-day all-cause mortality (Fisher, et al. (1994) supra; Abraham, et al. (1995) supra; Abraham, et al. (1998) supra; Opal, et al. (2004) supra). Details of these studies were thoroughly described in the articles that reported their results (Bone, et al. (1995) supra; Fisher, et al. (1994) supra; Abraham, et al. (1995) supra; Abraham, et al. (1998) supra; Opal, et al. (2004) supra; Dellinger, et al. (2004) *Crit. Care Med.* 32:858-873).

In NORASEPT, septic mortality was slightly reduced, but not significantly, among patients with shock at baseline who received the 7.5 mg/kg TNFMAb dosage (Abraham, et al. (1995) supra). In NORASEPT II, therefore, the investigators decided to randomize only patients with septic shock at baseline to either placebo or 7.5 mg/kg TNFMAb (Abraham, et al. (1998) supra). Because the enrollment criteria were otherwise identical, the two studies were considered sufficiently similar to use patient data from NORASEPT II to validate the SMART models developed on NORASEPT.

In the CORTICUS, E5, NORASEPT, IL-1ra, and the pre-interim analysis cohort of COMPASS, on HIPAA compliant, prerandomization clinical information from patients in each study for whom complete data sets were available, using multivariate, step-wise logistic regression with all ways elimination (simultaneous forward and backward elimination of nonweighted independent variables), SMART survival models were separately developed for the placebo and active drug groups. For the E5 study, SMART models also predicted drug effects on organ failure or death. Statistical significance at $p<0.10$ identified potential independent variables and was the threshold for testing them in the final equations, with, conversely, $p>0.10$ being the threshold for excluding a potential independent variable. These separate survival models for each study, generated separately from the placebo and from the active drug baseline, prerandomization databases, made it possible to test two possible probabilities for each individual patient: the probability of survival for that patient receiving the active study drug and placebo. After the modeling process was completed, prerandomization data from every patient in that study were entered into both equations, and lengthy explorations into the relationship between the placebo and active drug models and their interactions with treatment effects were undertaken to analyze optimum cutoffs for each drug. Beginning with the original consensus definition patient population, this process tested study drug treatment effects in progressively smaller subpopulations, incrementally excluding, always at prerandomization baseline, from each study's efficacy analysis patients whom SMART predicted would survive if they were to receive placebo and/or who would expire if they were to receive the active drug. This exploration was performed for each clinical trial on a theoretically infinite number of cutoff points, with efficacy in reducing septic mortality tested for each study drug in cohorts having mortality rates ranging from 0% to 100%. As patients who were excluded from efficacy analysis at each cutoff point were identified before randomization, the resulting placebo and active drug subgroups were, by definition, equal. With this approach, only subjects who were identified by the SMART models for each study as responsive to the treatment arm were included in outcomes statistics, thereby giving each drug a fair chance to prove its efficacy. Survival-treatment effects were evaluated separately among patients enrolled under consensus definitions and among patients predicted by SMART to respond to each sepsis drug. Mortality was analyzed by Kaplan-Meier statistics (SAS Institute (1994) SAS/STAT User's Guide, Version 6, $4^{th}$ Ed. Cary, N.C.) as were the E5 results for drug treatment effects on end-organ dysfunction. The E5 and Synergen 0509 results were retrospective, because the Synergen 0556 study database (Opal, et al. (1997) *Crit. Care Med.* 25:115-123) was not released, and the third phase III clinical trial of E5 versus placebo in sepsis had insufficient data to support the SMART models (Angus, et al. (2000) *JAMA* 283:1723-1730).

As prospective validation of the SMART models for the TNFMAb molecule, and of the efficacy of the drug, baseline information from NORASEPT II subjects was entered into SMART models from NORASEPT. Then, treatment effects of TNFMAb were assessed among consensus NORASEPT II patients, and, separately, in the SMART cohort.

In the COMPASS clinical trial PAF-AH, modeling was conducted on the 600 patients enrolled for the interim analysis. Then, PAF-AH versus placebo treatment effects were tested prospectively by entering data from the 623 subjects in the second COMPASS interim analysis cohort into the SMART models built upon the first interim group's data.

The $X^2$ equation (SAS Institute (1994) supra) was used to ensure that the distribution of baseline discrete variables was equal within each study for placebo versus active drug populations.

Example 2

Results Using SMART Models

Baseline parameters that were screened as possible independent variables for SMART models that were developed from the CORTICUS, E5, TNFMAb, IL-1ra, and PAF-AH clinical trial databases are listed in Table 2. Nearly, all these demographic, physiologic, clinical, and hospital laboratory data points were captured at prerandomization baseline in each study, always within 24 hours or less before administrations of the study drug. Nearly, all the variables listed were measured at prerandomization baseline in every patient, pursuant to FDA safety-monitoring requirements (Dellinger, et al. (2004) supra; Bone, et al. (1995) supra; Fisher, et al. (1994) supra; Abraham, et al. (1995) supra; Abraham, et al. (1998) supra; Opal, et al. (2004) supra).

TABLE 2

Baseline Observations

APACHE II score
Body surface area
Underlying comorbidities

TABLE 2-continued

Baseline Observations

Cardiovascular
Pulmonary disease
Autoimmune
Hematologic
Hepatic
Neurologic
Renal or bladder
Diabetes mellitus
Cancer
Other endocrine
Immunosuppressive therapy
Sex
Alcoholism
Simplified Acute Physiology
Score (SAPS)
Source of infection
    Urinary tract
    Lungs
    Intra-abdominal
    Wound
    Blood
    Central nervous system
    Indwelling catheter
    Other
    Causative microorganism
Diagnostic procedures
    Estimated sepsis severity
    Blood pressure: systolic,
        diastolic, mean
    Heart rate
    Respiratory rate
    Glasgow Coma Scale
Age
Days since admission
Blood work
    Serum Electrolytes
    Hemoglobin
    Hematocrit
    White blood cell count
    Platelets
    Arterial blood gas
    $FiO_2$
Estimated sepsis severity
Race
Major surgery/trauma
    Elective
    Emergency
Cardiac output
Sequential Organ Failure
Assessment (SOFA) score
Baseline organ failure
    Renal
    Acute respiratory distress
        syndrome (ARDS)
    Disseminated intravascular
        coagulation (DIC)
    Hepatobiliary
    Central nervous system
    Shock
Abnormal physical examination
    Neck
    Abdomen
    Skin
    Extremities
    Neurologic
    HEENT
    Respiratory
    Cardiovascular Independent variables that were weighted components of the SMART models built on the NORASEPT sepsis study are displayed in Table 3.

TABLE 3

| | Placebo Model | | TNFMab Model | |
|---|---|---|---|---|
| | p | Odds Ratio | p | Odds Ratio |
| NORASEPT | | | | |
| APACHE II Score | <0.001 | 1.089 | <0.001 | 1.116 |
| PTT | 0.02 | 1.016 | — | — |
| RBC | <0.001 | 0.473 | — | — |
| ROC AUC | 0.777 | | 0.737 | |
| NORASEPT II Prospectively validated models | | | | |
| ROC AUC | 0.727 | | 0.703 | |

SMART models that predicted 28-day all-cause mortality risk were generated separately from the placebo and active drug clinical trial databases, using prerandomization data.

TNFMAb versus placebo treatment effects on 28-day all-cause mortality for NORASEPT and NORASEPT II are respectively displayed in Tables 4 and 5.

TABLE 4

| | NORASEPT Consensus Definition Cohort (n = 623) | | SMART cohort (n = 205) | |
|---|---|---|---|---|
| | Placebo | TNFMAb | Placebo | TNFMAb |
| Total | 308 | 315 | 110 | 95 |
| Dead | 103 | 93 | 52 | 33 |
| Alive | 225 | 222 | 58 | 62 |
| Mortality (%) | 33.4 | 29.5 | 47.2 | 34.7 |
| Absolute* | 3.9 | | 12.6 | |
| Relative* | 11.7 | | 26.6 | |
| P* | | 0.20 | | 0.03 |

*Mortality reduction vs placebo (%).
SMART cohort was identified through analysis of interactions between study drug treatment effects and prerandomization placebo and active drug survival models.

TABLE 5

| | NORASEPT II Consensus Definition Cohort (n = 1741) | | SMART cohort (n = 744) | | Non-SMART Cohort (n = 997) | |
|---|---|---|---|---|---|---|
| | Placebo | TNFMAb | Placebo | TNFMAb | Placebo | TNFMAb |
| Total | 863 | 878 | 371 | 373 | 492 | 505 |
| Dead | 379 | 360 | 184 | 158 | 195 | 202 |
| Alive | 484 | 518 | 187 | 215 | 297 | 303 |
| Mortality (%) | 43.9 | 41.0 | 49.6 | 42.4 | 39.6 | 40.0 |
| Absolute* | 2.9 | | 7.2 | | 0 | |
| Relative* | 6.6 | | 14.5 | | 0 | |
| P* | | 0.15 | | 0.02 | | |

*Mortality reduction vs placebo (%).
SMART cohort was identified through analysis of interactions between study drug treatment effects and prerandomization placebo and active drug survival models.

For the 623 patients in NORASEPT, mortality was 33.4% placebo and 29.5% TNFMAb (3.9% absolute reduction; 11.7% relative to placebo; p=0.20). In the SMART cohort, placebo mortality was 47.3% and 34.7% TNFMAb (12.6% absolute; 26.9% relative to placebo; p=0.03). For NORASEPT II, mortality was 43.9% placebo and 41.0% TNFMAb (2.9% absolute; 6.6% relative to placebo; p=0.15). In the NORASEPT II SMART cohort, 28-d mortality was 49.6% placebo and 42.4% TNFMAb (7.2% absolute and 14.5% relative to placebo; p=0.02).

Independent variables in SMART models for E5 antiendotoxin antibody are displayed in Table 6.

TABLE 6

| Independent Variable | Odds Ratio Estimates - 95% Wald Confidence Limits |
|---|---|
| APACHE II Score | 1.039-1.144 |
| Urinary tract source of infection | 0.222-0.727 |
| Lung source of infection | 0.920-4.889 |
| Respiratory rate | 1.008-1.071 |
| Diastolic blood pressure | 0.951-0.987 |
| DIC | 1.344-16.808 |
| Age | 1.027-1.067 |
| Neurologic comorbidity | 1.341-5.185 |
| Acute CNS dysfunction | 0.140-0.517 |
| ARDS | 3.702-18.304 |
| Hepatobiliary dysfunction | 1.734-19.037 |

CNS, central nervous system.
SMART models that predicted 28-d all-cause mortality risk were generated separately from the placebo and active drug clinical trial databases, using prerandomization data.

Treatment effects on 30-day all-cause mortality for E5 versus placebo are displayed in Table 7.

TABLE 7

|  | Consensus Definition Cohort (n = 759) | | SMART cohort (n = 388) | |
|---|---|---|---|---|
|  | E5 | Placebo | E5 | Placebo |
| Total | 390 | 369 | 201 | 187 |
| Dead | 102 | 101 | 16 | 32 |
| Alive | 288 | 268 | 185 | 155 |
| Mortality (%) | 26.2 | 27.4 | 8.0 | 17.1 |
| Absolute* | 1.2% | | 9.1% | |
| Relative* | 4.4% | | 53.2% | |
| P* |  | 0.0747 |  | 0.006 |

*Mortality reduction vs. placebo (%).
SMART cohorts were identified through analysis of interactions between study drug treatment effects and prerandomization placebo and active drug survival models.

Organ failure/death in severe sepsis and septic shock for E5 versus placebo are displayed in Table 8.

TABLE 8

|  | E5 vs. Placebo p values | |
|---|---|---|
|  | Consensus cohort (n = 759) | SMART cohort (n = 388) |
| ARDS | 0.43 | 0.01 |
| Hepatobiliary | 0.65 | 0.03 |
| Renal | 0.81 | 0.22 |
| CNS | 0.20 | 0.02 |
| DIC | 0.54 | 0.002 |
| Shock | 0.97 | 0.04 |

SMART cohorts were identified through analysis of interactions between study drug treatment effects and prerandomization placebo and active drug survival models.

In the consensus E5 population, placebo mortality was 27.4% and E5 26.2% (1.2% absolute; 4.4% relative to placebo; p=0.747). In the E5 SMART cohort, placebo mortality was 17.1% and E5 8.0% (9.1% absolute; 53.2% relative to placebo; p<0.01).

Independent variables of SMART models from the Synergen 0509 clinical trial of IL-1ra in sepsis are displayed in Table 9.

TABLE 9

| Independent Variable | Odds Ratio Estimates-95% Wald Confidence Limits |
|---|---|
| Placebo model results (n = 302)* | |
| ARDS | 0.169-0.621 |
| DIC | 0.135-0.616 |
| Mean arterial pressure | 1.007-1.047 |
| Temperature | 1.082-1.634 |
| Arterial pH | 1.673-5.427 |
| BUN | 0.967-0.990 |
| $FiO_2$ | 0.990-0.999 |
| High-dose IL-1ra model results (n = 293)† | |
| Cardiovascular | 0.264-0.934 |
| Age | 0.965-0.998 |
| Systolic blood pressure | 1.003-1.034 |
| Respiratory infection | 0.288-0.895 |
| Urinary tract infection | 1.993-25.933 |
| BUN | 0.978-0.998 |
| Low-dose IL-1ra model results (n = 298)‡ | |
| ARDS | 0.193-0.738 |
| DIC | 0.138-0.595 |
| Acute Renal Failure | 0.215-0.708 |
| Vasco | 0.274-0.872 |
| Age | 0.956-0.989 |
| HEENT abnormal | 0.214-0.717 |
| Abdomen abnormal | 0.328-1.124 |
| Neurological abnormal | 0.361-1.119 |
| Extremities/joint abnormal | 0.320-1.009 |

*ROC AUC = 0.822.
†ROC AUC = 0.762.
‡ROC AUC = 0.776.
SMART models that predicted 28-d all-cause mortality risk were generated separately from the placebo and active drug clinical trial databases, using prerandomization data.

Treatment effects of IL-1ra versus placebo on 28-day all-cause mortality are displayed in Tables 10-12.

TABLE 10

|  | Consensus Definition Cohort | | |
|---|---|---|---|
|  | Placebo | Low Dose | High Dose |
| Total | 298 | 290 | 289 |
| Dead | 101 | 93 | 86 |
| Alive | 197 | 197 | 203 |
| Mortality (%) | 33.9 | 32.1 | 29.8 |
| Absolute* |  | 1.8 | 4.1 |
| Relative* |  | 4.3 | 12.1 |
| P* |  | 0.618 | 0.282 |

*Mortality change vs. placebo (%).
SMART cohorts were identified through analysis of interactions between study drug treatment effects and prerandomization placebo and active drug survival models.

TABLE 11

|  | SMART Cohort High Dose | | | | | |
|---|---|---|---|---|---|---|
|  | Placebo | High Dose | Placebo | High Dose | Placebo | High Dose |
| Total | 176 | 181 | 133 | 123 | 77 | 72 |
| Dead | 85 | 66 | 74 | 43 | 52 | 29 |
| Alive | 91 | 115 | 59 | 80 | 25 | 43 |
| Mortality (%) | 48.3 | 36.5 | 55.6 | 35.0 | 67.5 | 40.3 |

TABLE 11-continued

SMART Cohort High Dose

|  | Placebo | High Dose | Placebo | High Dose | Placebo | High Dose |
|---|---|---|---|---|---|---|
| Absolute* |  | 11.8 |  | 20.6 |  | 27.2 |
| Relative* |  | 24.4 |  | 37.1 |  | 40.3 |
| P* |  | 0.024 |  | 0.0009 |  | 0.0008 |

*Mortality change vs. placebo (%).
SMART cohorts were identified through analysis of interactions between study drug treatment effects and prerandomization placebo and active drug survival models.

TABLE 12

SMART Cohort Low Dose

|  | Placebo | Low dose | Placebo | Low dose |
|---|---|---|---|---|
| Total | 169 | 165 | 61 | 54 |
| Dead | 79 | 56 | 38 | 14 |
| Alive | 90 | 109 | 23 | 40 |
| Mortality (%) | 46.7 | 35.9 | 62.3 | 25.9 |
| Absolute* |  | 10.8 |  | 36.4 |
| Relative* |  | 23.1 |  | 58.4 |
| P* |  | 0.017 |  | <0.0001 |

*Mortality change vs. placebo (%).
SMART cohorts were identified through analysis of interactions between study drug treatment effects and prerandomization placebo and active drug survival models.

In sepsis syndrome patients (n=877), mortality was 33.9% placebo, 32.1% for 1.0 mg/kg/h IL-1ra (1.8% absolute; 5.3% relative; p=0.6178), and 29.8% for IL-1ra 2.0 mg/kg/h (4.1% absolute; 12.1% relative; p=0.2824). In one SMART cohort (59.2%/62.6% of placebo/IL-1ra consensus populations), placebo mortality was 48.3%, versus IL-1ra, at 2.0 mg/kg/h, 36.5% (11.8% absolute; 24.4% relative; p=0.024). In a more IL-1ra-specific SMART cohort (44.6%/42.6% of placebo/IL-1ra consensus populations), placebo mortality was 55.6% versus 35.0% IL-1ra (20.6% absolute; 37.1% relative; p<0.001). In a third SMART cohort (25.8%/24.9% of placebo/IL-1ra consensus populations), placebo mortality was 67.5% versus 40.3% IL-1ra (27.2% absolute; 37.1% relative; p<0.001).

For IL-1ra 1.0 mg/kg/h, in a SMART cohort (56.7%/56.9% of placebo/IL-1ra consensus populations), placebo mortality was 46.7% versus 35.0% IL-1ra (10.8% absolute; 23.1% relative; p=0.017). Another SMART cohort (20.5%/18.6% of placebo/IL-1ra consensus populations) had placebo mortality 62.3% versus 25.9% IL-1ra (36.4% absolute; 58.4% relative; p<0.0001).

Independent variables for SMART models from the ICOS COMPASS clinical trial are listed in Table 13.

TABLE 13

| Independent Variable | Odds Ratio Estimates-95% Wald Confidence Limits |
|---|---|
| Placebo* |  |
| Mechanical ventilator | 0.066-0.412 |
| APACHE II score | 1.049-1.171 |
| Multiple organ dysfunction score | 1.006-1.306 |
| Eosinophil count | 0.004-0.062 |

TABLE 13-continued

| Independent Variable | Odds Ratio Estimates-95% Wald Confidence Limits |
|---|---|
| PAF-AH† |  |
| Mechanical ventilator | 0.066-0.412 |
| Multiple organ dysfunction score | 1.006-1.171 |

*ROC AUC = 0.708.
†ROC AUC = 0.788.
SMART models that predicted 28-d all-cause mortality risk were generated separately from the placebo and active drug clinical trial databases, using prerandomization data.

PAF-AH versus placebo treatment effects on 28-day all-cause mortality are displayed in Tables 14 and 15.

TABLE 14

COMPASS I Clinical Trial

|  | Consensus Definition Cohort (n = 587) | | SMART Cohort I (n = 251) | |
|---|---|---|---|---|
|  | Placebo | PAF-AH | Placebo | PAF-AH |
| Total | 304 | 283 | 130 | 121 |
| Dead | 68 | 65 | 23 | 35 |
| Alive | 236 | 218 | 107 | 86 |
| Mortality (%) | 22.4 | 22.9 | 17.7 | 28.9 |
| Absolute* |  | 0.5 |  | 11.2 |
| Relative* |  | 2.2 |  | 63.3 |
| P* |  | 0.921 |  | 0.039 |

*Mortality change vs. placebo (%).
SMART cohorts were identified through analysis of interactions between study drug treatment effects and prerandomization placebo and active drug survival models.

TABLE 15

COMPASS II Clinical Trial

|  | Consensus Definition Cohort (n = 540) | | SMART Cohort II (n = 244) | |
|---|---|---|---|---|
|  | Placebo | PAF-AH | Placebo | PAF-AH |
| Total | 255 | 285 | 119 | 125 |
| Dead | 66 | 73 | 38 | 27 |
| Alive | 189 | 212 | 81 | 98 |
| Mortality (%) | 25.9 | 25.6 | 31.9 | 21.6 |
| Absolute* |  | 0.3 |  | 10.3 |
| Relative* |  | 1.1 |  | 32.3 |
| P* |  | 1.000 |  | 0.0551 |

*Mortality change vs. placebo (%).
SMART cohorts were identified through analysis of interactions between study drug treatment effects and prerandomization placebo and active drug survival models.

In the consensus COMPASS population (COMPASS I), placebo mortality was 22.4% versus 22.9% for PAF-AH (0.5% absolute survival increase; 2.2% relative; p=0.924). The SMART cohort of COMPASS I had placebo mortality 17.7% versus PAF-AH 28.9% (11.2% absolute increase in septic mortality versus placebo; 63.3% relative; p=0.039). The COMPASS I SMART models and PAF-AH treatment effects were tested prospectively on the COMPASS II population that followed COMPASS 1 up to the second and final interim analysis. In the COMPASS II consensus population (n=540), placebo mortality was 25.9% versus 25.6% for PAF-AH. In the SMART COMPASS II cohort (n=244), placebo mortality was 31.9% versus 21.6% for PAF-AH (10.3% absolute reduction in mortality; 32.3% relative; p=0.0551).

Independent variables that were weighted components of the SMART models built on the CORTICUS sepsis study are listed in Tables 16 (placebo model) and 17 (treatment model). There were 500 patients in the CORTICUS database. Due to missing values and values in error, there were only 446 (89%) patients that were analyzable.

TABLE 16

| Parameter | Estimate (Std. Error) | Wald Chi-Square | p-value | Point Estimate | Odds Ratio Estimates - 95% Wald Confidence Limits |
|---|---|---|---|---|---|
| Intercept | −4.0449 (0.7431) | 29.6260 | <0.0001 | | |
| Hypertension | 0.6384 (0.3100) | 4.2401 | 0.0395 | 1.893 | 1.031-3.476 |
| Respiratory Rate | 0.0441 (0.0169) | 6.8249 | 0.0090 | 1.045 | 1.011-1.080 |
| SAPS | 0.0411 (0.0105) | 15.1477 | <0.0001 | 1.042 | 1.042-1.021 |

N = 224;
AUC = 0.714.

TABLE 17

| Parameter | Estimate (Std. Error) | Wald Chi-Square | p-value | Point Estimate | Odds Ratio Estimates - 95% Wald Confidence Limits |
|---|---|---|---|---|---|
| Intercept | −6.9042 (1.2726) | 29.4342 | <0.0001 | | |
| Age | 0.0421 (0.0128) | 10.7968 | 0.0010 | 1.043 | 1.017-1.069 |
| PaCO2 High mmHg | 0.0460 (0.0145) | 10.0603 | 0.0015 | 1.047 | 1.018-1.077 |
| BE low mmol l | −0.0741 (0.0272) | 7.4116 | 0.0065 | 0.929 | 0.880-0.979 |
| 24 before Total SAPS | 0.0237 (0.00956) | 6.1457 | 0.0132 | 1.024 | 1.005-1.043 |

N = 222;
AUC = 0.734.

Hydrocortisone versus placebo treatment effects for CORTICUS patients are displayed in Table 18.

TABLE 18

| | Consensus Definition Cohort (n = 446) | | SMART Cohort (n = 421) | | Non-SMART Cohort (n = 25) | |
|---|---|---|---|---|---|---|
| | Placebo | HC | Placebo | HC | Placebo | HC |
| Total | 224 | 222 | 212 | 209 | 12 | 13 |
| Alive | 153 | 144 | 148 | 141 | 5 | 3 |
| Dead | 71 | 78 | 64 | 68 | 7 | 10 |
| Mortality (%) | 31.70 | 35.14 | 30.19 | 32.54 | 58.33 | 76.92 |
| Absolute* | | −3.44 | | −2.35 | | |
| Relative* | | −10.85 | | −7.78 | | |
| P* | | 0.6019 | | 0.1696 | | 0.2636 |

*Mortality change vs. placebo (%).
HC, hydrocortisone.
SMART cohorts were identified through analysis of interactions between study drug treatment effects and prerandomization placebo and active drug survival models.

Independent variables that were weighted components of the SMART models built on the corticotrophin non-responder database of CORTICUS are listed in Tables 19 (placebo model) and 20 (treatment model).

TABLE 19

| Parameter | Estimate (Std. Error) | Wald Chi-Square | p-value | Point Estimate | Odds Ratio Estimates - 95% Wald Confidence Limits |
|---|---|---|---|---|---|
| Intercept | −3.3199 (0.7857) | 17.8538 | <0.0001 | | |
| CRF | 1.2364 (0.7035) | 3.0882 | 0.0789 | 3.443 | 0.867-13.671 |
| SAPS | 0.0439 (0.0136) | 10.4859 | 0.0012 | 1.045 | 1.017-1.073 |

N = 107;
AUC = 0.728.

TABLE 20

| Parameter | Estimate (Std. Error) | Wald Chi-Square | p-value | Point Estimate | Odds Ratio Estimates - 95% Wald Confidence Limits |
|---|---|---|---|---|---|
| Intercept | 75.8534 (25.2130) | 9.0511 | 0.0026 | | |
| SAPS | 0.0587 (0.0172) | 11.6183 | 0.0007 | 1.060 | 1.025-1.097 |
| Temperature | −0.8936 (0.2700) | 10.9555 | 0.0009 | 0.409 | 0.241-0.695 |
| Norepinephrine | 2.4155 (0.8313) | 8.4438 | 0.0037 | 11.196 | 2.195-57.101 |
| pH low | −6.4081 (2.8372) | 5.1013 | 0.0239 | 0.002 | <0.001-0.429 |
| Hypertension | 1.0664 (0.5373) | 3.9387 | 0.0472 | 2.905 | 1.013-8.327 |

N = 108;
AUC = 0.866.

Hydrocortisone versus placebo treatment effects of septic shock survival among CORTICUS patients who did not respond to corticotrophin are tabulated in Table 21.

TABLE 21

| | Consensus Definition Cohort (n = 216) | | SMART Cohort (n = 168) | | Non-SMART Cohort (n = 38) | |
|---|---|---|---|---|---|---|
| | Placebo | HC | Placebo | HC | Placebo | HC |
| Total | 96 | 119 | 82 | 86 | 14 | 24 |
| Dead | 66 | 66 | 57 | 63 | 9 | 3 |
| Alive | 30 | 44 | 25 | 23 | 5 | 21 |
| Mortality (%) | 31.25 | 40.00 | 30.49 | 26.74 | 35.71 | 87.50 |
| Absolute* | | −8.75 | | 3.75 | | |
| Relative* | | −28 | | 12.3 | | |
| P* | | 0.3209 | | 0.2973 | | |

*Mortality change vs. placebo (%).
HC, hydrocortisone.
SMART cohorts were identified through analysis of interactions between study drug treatment effects and prerandomization placebo and active drug survival models When all CORTICUS patients were included in analyses, among consensus septic shock patients, hydrocortisone mortality was 35.14%, compared with placebo mortality 31.7% (p=0.6019). In the overall SMART cohort from CORTICUS, hydrocortisone and placebo moralities were 43.54 and 30.19, respectively (p=0.1696). Among corticotropin non-responders, overall hydrocortisone/placebo mortality was 40.0%/31.25%, respectively, an −8.75% adverse hydrocortisone treatment effect (p=0.3209). In the SMART coticotropin non-responder group, hydrocortisone/placebo mortality was 26.74% versus 30.49%, respectively (p=0.2973).

There were few weighed independent variables that were common between the five clinical trials in the SMART placebo models. Placebo models from the IL-1ra and E5 studies had disseminated intravascular coagulation (DIC) and acute respiratory distress syndrome (ARDS) as significantly weighted independent variables. APACHE (Acute Physiology and Chronic Health Evaluation) II score was common to the NORASEPT and COMPASS clinical trials. No other independent variables factored significantly in more than one SMART placebo model.

Example 3

Application of SMART Models

In the XOMA E5 sepsis clinical trial, SMART discovered patients among whom E5 not only improved survival but also reduced organ failure. Subjects enrolled by consensus definitions alone received only a nonsignificant 1.4% absolute survival benefit from E5. In the SMART cohort, however, which included 51% of the consensus population, E5 reduced mortality by 9.1% absolute, 53.2% relative to placebo. In the SMART cohort, placebo mortality was only 17.1%, more than 10% lower than in the parent consensus definition population. Logically, one might expect gram-negative infection to have been a weighted independent variable in SMART models for an anti-endotoxin antibody, but infecting bacteriology did contribute to these equations. On the surface, these findings also seem inconsistent with the results of the MEDIC study (Marshall, et al. (2004) *J. Infect. Dis.* 190:527-534), which reported strong correlations between increased circulating endotoxin levels and high APACHE II, MOD, and SOFA scores, shock, decreasing partial pressure of oxygen in arterial blood/fractional inspired oxygen ratio, and leucopenia or leukocytosis. The results of this study, specifically the finding of E5-responsive patients in a lower mortality subgroup, presumably, therefore, with low-circulating endotoxin (Marshall, et al. (2004) supra), suggest that endotoxin levels alone might not predict treatment effects for anti-endotoxin strategies. It may be that E5 succeeded here by SMART's incorporating the septic pathophysiology of individual patients into the subject selection data mix.

Another interesting observation was that E5 reduced septic mortality only in lower acuity patients, with placebo mortality only 17.1%. This contrasts strikingly with the results of the Phase 2 trial of eritoran tetrasodium (E5564), a toll-like receptor 4 antagonist that interferes with endotoxin signaling (Tidswell, et al. (2010) *Crit. Care Med.* 38:72-83). In that investigation, a nonsignificant trend toward lower septic mortality was seen in high-dose eritoran subjects with high APACHE II predicted risk of mortality. These results indicate that for each truly effective molecule in sepsis therapy, there are patients whose host-inflammatory responses to infection are matched biologically to that drug, and who, therefore, are specifically able to benefit from it. Apparently, even different anti-endotoxin interventions have different target populations. It follows, logically, then, that the true target populations for different sepsis therapies should vary significantly, according to the mechanism of action of each molecule. The low mortality therapeutic niche identified here for E5 could be confirmed prospectively. Unfortunately, the third E5 sepsis investigation did not capture data sufficient to support the E5 SMART models, and the SMART uncovered also a significant E5 treatment effect on organ failure. Although E5 had no significant effects on organ failure or shock in the consensus population, among SMART E5 responders, ARDS, hepatobiliary failure, cerebral dysfunction, DIC, and shock were reduced dramatically findings here, therefore, could not be validated prospectively (Opal, et al. (1997) *Crit. Care Med.* 25:115-123).

A clinically significant discovery of this investigation was the unprecedented, extremely high reduction of septic mortality among SMART patients by IL-1ra. Compared with the sepsis syndrome population, in which high-dose IL-1ra reduced mortality by only 4.1% versus placebo, among patients identified by SMART as able to benefit from the study drug, IL-1ra improved survival by from 9% up to 50% absolute, in increasingly IL-1ra-specific cohorts. Such dramatically increased septic survival has not been reported for any other drug ever tested in humans. Unfortunately, the SYNERGEN 0556 sepsis clinical trial of IL-1ra (Angus, et al. (2000) *JAMA* 283:1723-1730), which followed the 0509 study and was nearly identical to it, was not made available to validate prospectively the SMART/IL-1ra models and the IL-1ra efficacy in sepsis seen here. Considering the life-saving potential of IL-1ra seen here, clinical development of this drug for sepsis should be revisited.

Results of SMART retrospective, post hoc analyses in sepsis, and the efficacy of successful drugs, should be validated prospectively in populations of like patients who were not included in the equation-building process. This was accomplished for SMART models based on NORASEPT. In the post hoc phase, survival benefits of TNFMAb in NORASEPT were improved from 3.9% in consensus patients, to 12.6% in the SMART-identified cohort. Then, baseline raw data from NORASEPT II patients was entered into the SMART equations from NORASEPT. In the SMART cohort of NORASEPT II, TNFMAb lowered septic shock mortality significantly, as it had done in NORASEPT SMART group. These results validated prospectively the predictive power of SMART models from NORASEPT and established TNFMAb efficacy in reducing septic mortality.

SMART prognostic models from the population of the first interim analysis of the COMPASS study of PAF-AH in sepsis also were validated prospectively, using the second and final interim analysis cohort of that clinical trial. Septic mortality was increased significantly compared with placebo among active PAF-AH subjects in the SMART modeling cohort of COMPASS. When data from subjects of the second COMPASS interim analysis group were entered into the SMART models, increased PAF-AH mortality was not confirmed, but, conversely, neither was a significant beneficial effect identified. One might speculate that application of the SMART approach to the first interim analysis data of COMPASS would have resulted in termination of that investigation earlier, with significant savings of research dollars, and, possibly, of adverse drug effects among study subjects.

The addition of SMART statistical analysis to the CORTICUS clinical trial database did not identify a sub-population of CORTICUS patients among whom hydrocortisone reduced septic shock mortality. Rather, in the overall CORTICUS population, the 3.4% increased mortality of the hydrocortisone arm, versus placebo, was reduced immeasurably to a negative 2.5% among the best hydrocortisone-responsive group SMART could find. Among the CORTICUS target cohort of patients in septic shock who did not respond to corticotropin adrenal stimulation, and who, theoretically, would be responsive to stress doses of exogenous steroids, in consensus definition septic shock patients, the mortality rate was 8.75% higher in the hydrocortisone arm than in the placebo group. While SMART models generated from the CORTICUS corticotrophin non-responders identified patients among whom hydrocortisone did improve septic shock survival by 3.75%, this was not a statistically significant treatment advantage. In the face of SMART uncovering groups of individual septic patients within the E5, TNFMAb and IL-1-ra clinical trials wherein each of these drugs reduced septic mortality significantly, one must conclude that hydrocortisone, even when matched to septic shock patients who may be most responsive to it, has no salubrious effect on the death rate in sepsis. Considering in addition the previous reports of increased adverse effects of these drugs in sepsis, including super-infections and augmented mortality with renal failure (Bone, et al. (1987) *New Engl. J. Med.* 317:653-59; The veterans Administration Systemic Sepsis Cooperative Study Group (1987) *New Engl. J. Med.* 317:659-655), the results of this study indicate that corticosteroids are not effective adjuvant regimens in septic shock.

From this study, SMART can be used to facilitate clinical development of new therapeutic molecules for sepsis, such as other anti-TNF strategies (Pulmonary Reviews.com (2000) supra; Rice, et al. (2006) *Crit. Care Med.* 34:2271-2281) anti-endotoxin interventions (Bone, et al. (1995) *Crit. Care Med.* 23:994-1006; Tidswell, et al. (2010) *Crit. Care Med.* 38:72-83; Greenman, et al. (1991) *JAMA* 266:1097-1102) PAF interventions (Dhainaut, et al. (1995) *Abst. Am. J. Respir. Crit. Care Med.* 151:A447; Dhainaut, et al. (1997) *Crit. Care Med.* 25:115-123) or restoring coagulation homeostasis (Bernard, et al. (2001) supra), among others. SMART equations derived from Phase II databases could facilitate protocol development for Phase III clinical trials of novel therapies. Similarly, SMART evaluation of completed Phase III investigations could assist in confirmatory study design. Ultimately, SMART interactions with novel drugs may be able to guide bedside management of septic patients, supplemental to clinical judgment and consensus sepsis definitions screening.

Considering the multiple clinical trials testing IL-ra, anti-endotoxin, and anti-TNF regimens that have failed to reduce septic mortality (Pulmonary Reviews.com (2000) supra; Bone, et al. (1995) supra; Fisher, et al. (1994) *JAMA* 271:1836-1843; Abraham, et al. (1995) *JAMA* 273:934-941; Abraham, et al. (1998) *Lancet* 351:929-932; Opal, et al. (2004) supra; Rice, et al. (2006) supra), the results of this investigation indicate that enrollment criteria for such studies should be reconsidered. Certainly, the concept of designing a confirmatory clinical trial on the basis of subgroup analysis from a previous study has been discredited. This is evidenced in the failure of NORASEPT II (Abraham, et al. (1998) supra), wherein shock was added at entry, based on a nonsignificant trend toward anti-TNF efficacy observed in the preceding NORASEPT investigation (Abraham, et al. (1995) supra). In the sequential clinical trials of the E5 antibody, a trend toward efficacy among patients without shock in the first study led to excluding shock in the second study (Bone, et al. (1995) supra; Greenman, et al. (1991) supra). The second IL-1ra sepsis clinical trial (Angus, et al. (2000) *JAMA* 283:1723-1730) added organ failure and increased APACHE III risk of death as entry criteria, because post hoc analysis suggested a correlation between them and drug treatment responses. All three studies failed to reduce septic mortality. Similarly, severity of illness scores, including APACHE II scoring (Bernard, et al. (2001) supra; Tidswell, et al. (2010) *Crit. Care Med.* 38:72-83), and/or the presence of DIC (Abraham, et al. (1995) supra) or ARDS (Pittet, et al. (1999) *Am. J. Respir. Crit. Care med.* 160:852-857), while attractive as single, commonly understood screening measurements, also have not panned out as patient identification tools for predicting anti-TNF and anti-endotoxin treatment responses. Even though APACHE II was an independent variable in SMART survival models for both the E5 and TNFMAb populations, and DIC, and ARDS figured in the E5 SMART modeling, they contributed only to building the tools that identified individual septic pathophysiology. None of these factors directly predicted treatment response. Therefore, as the Cyto-Fab anti-TNF molecule (Rice, et al. (2006) supra) and eritoran tetrasodium (Tidswell, et al. (2010) supra) move from Phase II studies to Phase III confirmatory clinical trials, SMART finds application in supplementing patient identification if standard clinical definitions of sepsis, severity of illness, shock, DIC, or ARDS are to be entry criteria.

SMART may identify also patients for whom sepsis study drugs are ineffective, or even detrimental. During the current study, this was manifested in the preinterim analysis cohort of the COMPASS clinical trial (Opal, et al. (2004) supra), wherein PAF-AH increased septic mortality significantly among a SMART-predicted group. One might speculate that if SMART had been applied to the Phase II PAF-AH database, or even at the first Phase III interim analysis, then COMPASS could have been ended earlier, saving hundreds of subjects from the risk of possible adverse clinical effects.

The results of this study reiterate that the traditional definitions of severe sepsis and septic shock (Bone, et al. (1987) supra; Bone, et al. (1989) supra; Bone, et al. (1992) supra), when used as entry criteria for clinical trials, do not match responsive patients with study drugs that are biologically appropriate to their host pathophysiologies. Therefore, under consensus definition enrollment, new therapies for sepsis are denied a fair chance to prove their efficacy. So many patients are enrolled who would recover on placebo, and who would expire even on active drug, that the true treatment effects of even the most potent sepsis drugs are diluted. Good drugs fail because they are studied in the wrong patients. Then, they are abandoned by the pharmaceutical industry and never reach biologically appropriate patients whom they might save. After nearly three decades of clinical trials that failed because patients were entered through consensus definitions of sepsis, SMART now provides an alternative approach to selecting subjects for these studies.

SMART is an analytic approach that uses conventional statistical techniques and is applicable universally across the gamut of sepsis clinical trials. SMART can be used alone or as a supplement to consensus sepsis definitions given the prevalence of consensus criteria in sepsis clinical trials. Because each novel intervention for sepsis has its own unique mechanism of action, it follows that the host biology of treatment-responsive patients also is unique for each molecule. Therefore, weighted independent variables in the SMART models for E5, for example, are not the same as those for TNFMAb, IL-1ra, or PAF-AH. In addition, clinical factors that would seem to have obvious relevance to sepsis or to a specific drug, such as age, illness acuity, shock, or microbiology, might not pan out as significant independent variables in SMART modeling. Rather, by avoiding preconceived notions of which parameters might predict treatment success, SMART allows the host-inflammatory response to infection of each patient to interact with study drug mechanism of action, thereby building predictive models that match patients to drugs, accurately and objectively. Thus, by the very nature of the SMART approach, SMART is a dynamic process that ferrets out the important temporal interactions within each clinical trial database. The results of this study indicate that the SMART approach works across a variety of therapeutic agents in sepsis clinical trials.

Interestingly, the independent variables for the placebo survival models also varied considerably among the clinical trials analyzed in this study. One might expect, logically, that, at least the placebo patients from different sepsis investigations would be similar, statistically. However, one must realize that sepsis clinical trial entry criteria, while similar in concept, were not uniform in specifics among the studies analyzed here. Thus, NORASEPT, E5, IL-1ra, and COMPASS placebo survival models required varying independent variables, secondary to actual clinical differences in the study populations.

The results here demonstrate SMART's ability to identify objectively patients who can benefit from novel interventions in severe sepsis and septic shock, using readily available prerandomization clinical information, Given the results herein, SMART is also of use in developing predictive models for patients who can respond to molecules that currently are in active clinical development. Whether those models are built on Phase II databases, or as retrospective analyses of completed Phase III clinical trials, when they are used in subsequent confirmatory investigations, it is expected that SMART will give good drugs a fair chance to demonstrate efficacy in sepsis. Moreover, when treatments come into clinical use, SMART finds use in guiding physicians at the bedside, supplemental to consensus sepsis definition screening and to clinical judgment, toward optimizing their efficacy among septic patients in real time.

What is claimed is:

1. A method for identifying a subject whose host-inflammatory responses to a systemic inflammatory condition are matched to the mechanism of action of a therapeutic agent for the treatment of the subject comprising:

(a) obtaining one or more baseline parameters of a subject with a systemic inflammatory condition, wherein said baseline parameters comprise one or more demographic variables, physiologic variables, or results of hospital laboratory tests;
(b) generating, on a computer, from the baseline parameters, a systemic mediator-associated response test (SMART) profile for the subject;
(c) using statistical tests to compare the SMART profile of the subject with one or more control SMART profiles comprising independent variables for subjects who have responded positively to a therapeutic agent with a predetermined mechanism of action;
(d) identifying whether the SMART profile of the subject has independent variables of the control SMART profile for the therapeutic agent with a predetermined mechanism of action;
(e) selecting the therapeutic agent with the predetermined mechanism of action and treating the subject.

2. The method of claim 1, wherein the predetermined mechanism of action of the therapeutic agent is to inhibit tumor necrosis factor, inhibit endotoxin activity, inhibit interleukin-1 receptor, or degrade platelet-activating factor and oxidized phospholipids.

3. The method of claim 1, wherein the subject is being treated for a systemic inflammatory condition.

4. The method of claim 1, wherein the subject is in or being considered for a clinical trial.

* * * * *